United States Patent [19]

Gilson et al.

[11] 4,369,781
[45] Jan. 25, 1983

[54] LUER CONNECTOR

[75] Inventors: Richard W. Gilson, Dellwood, Mo.; Edward F. Windischman, Waterbury, Conn.

[73] Assignee: Sherwood Medical Industries Inc., St. Louis, Mo.

[21] Appl. No.: 233,540

[22] Filed: Feb. 11, 1981

[51] Int. Cl.³ .................... A61M 5/00; F16L 25/00; F16L 35/00
[52] U.S. Cl. .................... 128/214 R; 128/247; 285/332; 285/340
[58] Field of Search .......... 128/214, 247, 348, 214.2, 128/221, 334 C; 285/332, 331, 340

[56] References Cited

U.S. PATENT DOCUMENTS

| 1,668,315 | 5/1928 | Hein . | |
| 2,880,722 | 4/1959 | Dickinson, Jr. . | |
| 3,402,714 | 9/1968 | Higgins et al. | 128/221 |
| 3,514,131 | 5/1970 | McKinney | 285/332 |
| 3,585,996 | 6/1971 | Reynolds et al. | 128/214.4 |
| 3,633,944 | 1/1972 | Hamburg | 285/340 |
| 3,876,234 | 4/1975 | Harms | 285/332 X |
| 4,013,310 | 3/1977 | Dye | 285/110 |
| 4,073,514 | 2/1978 | Pate | 285/340 X |
| 4,133,312 | 1/1979 | Burd | 128/214 R |
| 4,187,848 | 2/1980 | Taylor | 128/247 |

Primary Examiner—Stephen C. Pellegrino
Attorney, Agent, or Firm—Stanley N. Garber; William R. O'Meara

[57] ABSTRACT

A fluid coupler for connecting two devices in locked fluid communication is provided which includes a body (12) having a male Luer lock connector (14) at one end connected in fluid communication with a female connector (28) at the other end. The female connector (28) is radially spaced from an outer wall (32) of the body (12) and has a Luer tapered bore (30) for receiving a male Luer tapered connector (62, 86) and a resilient locking member (40) connected to the body (12) at the other end thereof for frictionally engaging and locking the male Luer connector (62, 86) when inserted into the Luer tapered bore (30) to ensure against any subsequent fluid leakage between the connector.

9 Claims, 4 Drawing Figures

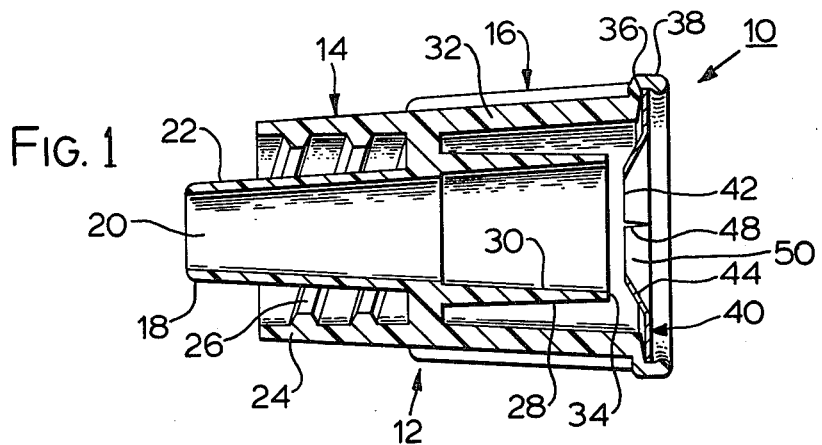
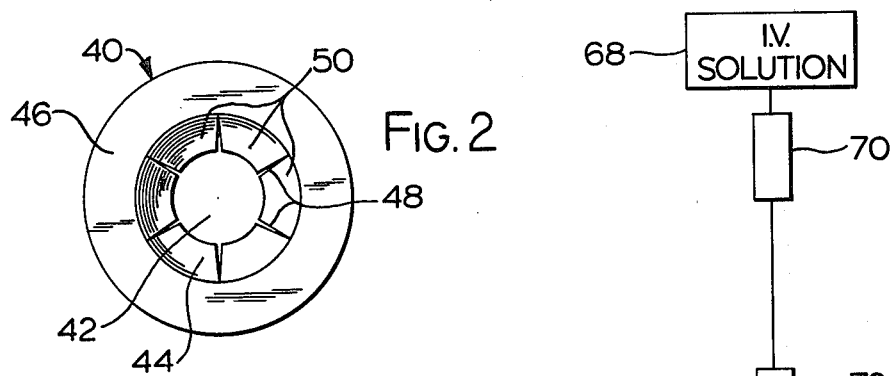
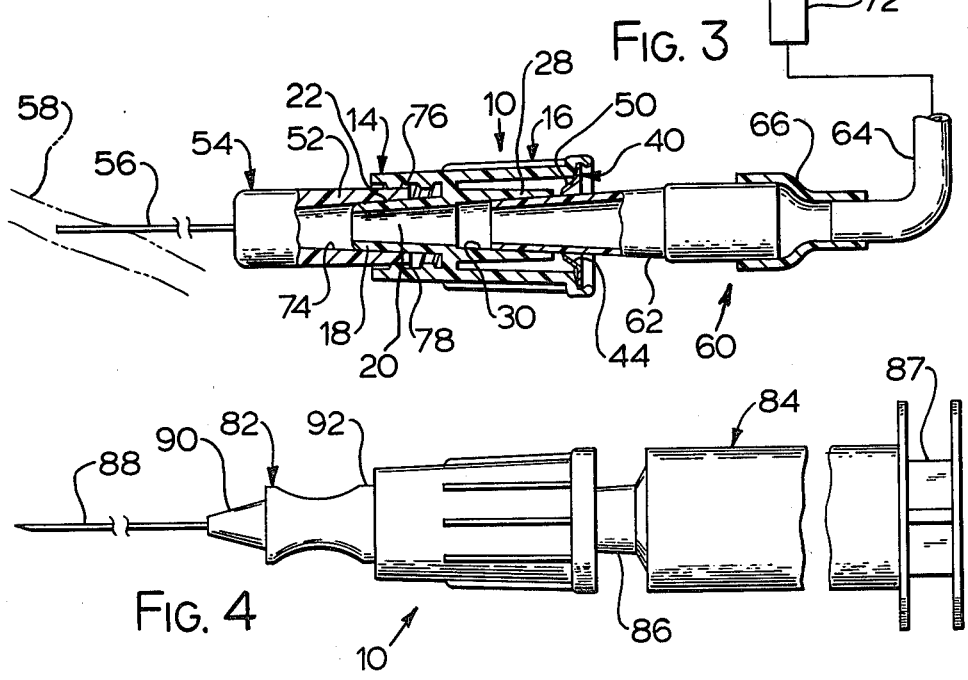

LUER CONNECTOR

TECHNICAL FIELD

This invention relates to Luer connectors and more particularly to a Luer connector of the locking type.

BACKGROUND ART

Standard Luer slip connectors are used extensively in the medical field to interconnect fluid passages of various medical devices. For example, in intravenously supplying liquids to patients, a supply tube is generally connected to the hub of a cannula disposed in the vein of a patient by a Luer slip connection. Also, some syringes have Luer slip tips for receiving the Luer slip hub of a needle cannula.

One of the problems associated with the use of Luer slip fluid connections is the danger that the connection may fail due to the application of inadvertent forces tending to pull the connection apart, such as may occur because of movement of the patient. This danger is increased in cases where the Luer slip connection is to be maintained over an extended period of time, such as when medicaments are intravenously supplied to a patient. Another problem is that a slip connection between a needle hub and a syringe tip may separate because a high fluid pressure may be developed during use of the syringe, and especially where the Luer slip connection was not made as tight as desirable.

Many medical devices are manufactured with Luer lock connectors which ensure fluid tight connections between devices. However, because of the added cost of such devices and because such Luer locking connectors are not needed or required in many applications, many devices do not have Luer lock connectors. For this reason, Luer slip connectors are sometimes used although Luer lock connectors would be desired and, in such cases, greater care and monitoring are required to insure good continuous connections.

DISCLOSURE OF THE INVENTION

The present invention is directed to overcoming one or more of the problems set forth above and has for its object to provide an improved connector which can be used to connect devices in fluid tight locked connection.

In accordance with one aspect of the present invention, a fluid coupler is provided which includes a body having a bore, connection means at one end for connecting a first device to the bore, and a connector at the other end having a Luer tapered bore for connecting a male Luer slip connector with the bore, and a resilient locking member for frictionally engaging and locking the male Luer slip connector against movement.

These, as well as other objects and advantages of the present invention, will become apparent from the following detailed description and drawing.

BRIEF SUMMARY OF THE INVENTION

FIG. 1 is a cross-sectional side view of a connector in accordance with a preferred embodiment of the present invention;

FIG. 2 is a plan view of the locking member of the connector of FIG. 1;

FIG. 3 is a side elevation partly in section, illustrating an infusion set employing the connector of FIG. 1; and FIG. 4 is a side elevation of a hypodermic syringe employing the connector of FIG. 1.

BEST MODE FOR CARRYING OUT THE INVENTION

Referring now to the drawings, and more particularly to FIG. 1, there is shown a fluid coupler or connector 10 which includes a body 12 having a fluid connector 14 at the left or distal end and a fluid connector 16 at the right or proximal end. The body 12 is formed of a suitable plastic such as polypropylene, polyethylene or the like.

The connector 14 is a well known Luer lock connector which includes a male Luer slip connector 18 having a bore 20 and an outer surface 22 tapered at a conventional Luer angle (3° 26′ 12″), and a concentric Luer lock collar 24 having internal locking threads 26. The male Luer lock connector 14 is adapted for connection with a conventional or standard female Luer lock connector, as will be discussed hereafter.

The connector 16 includes a hollow female Luer slip connector 28 having an inner Luer tapered bore or slip surface 30 adapted to receive a conventional or standard male Luer slip connector in frictional fluid tight connection. The connector 16 includes an outer generally cylindrical wall 32 radially spaced from and concentric with female slip connector 28 and which extends rightwardly or proximally of the distal end 34 of connector 28. The right end of wall 32 has an annular recess providing a shoulder 36 and an axially extending peripheral rim 38 in which is disposed an annular locking member 40.

The locking member 40, as seen also in FIG. 2, is shown as a generally disc-shaped member of resilient metal, such as stainless steel, having a central opening 42. Member 40 has a tapered or generally conical portion 44 extending around the opening 42 and a flat annular outer peripheral portion 46. The conical portion 44 is provided with a plurality of generally radial slots 48 extending outwardly from the opening 42 to the outer flat portion 46. Six equally spaced slots 46 are shown in FIG. 2. The slots 48 form six similar resilient arcuate fingers 50 between adjacent slots.

In assembling the locking member 40 to body 12, the member 40 may be placed within rim 38 against shoulder 36 and then the end of the rim swaged over an outer peripheral marginal area of the locking member as shown in FIG. 1 to secure it in place. The member 40 could alternately be secured in place by heat forming the rim over a portion of the member 40 or by other means.

The locking member 40 is secured in place against the shoulder 36 with the conical portion 44 inclined inwardly of the body toward Luer connector 28 and with the opening 42 coaxial or aligned with the Luer tapered bore 30. The opening 42 has a smaller diameter than the right or proximal end of bore 30. The longitudinal axis of the connector 18, collar 24, connector 28, wall 32 and member 40 are coincident.

The fluid coupler 10 can be used to positively connect a plastic, male Luer slip connector to a female Luer lock connector. For example, in FIG. 3 the coupler 10 is shown connected with a conventional or standard female Luer lock connector 52 of an infusion catheter 54 having a cannula 56 disposed in a vein 58 of a patient.

The fluid coupler 10 connects the catheter 54 in locked fluid communication with an intravenous (IV) solution system indicated schematically at 60. The IV system includes a male Luer lock slip connector 62, (without a Luer lock collar) inserted into the connector 16 of coupler 10 to connect the infusion catheter 54 with I.V. tube 64. Connector 62 is made of a suitable plastic, such as polypropylene. The tube 64 is connected to the Luer slip connector 62 by a resilient tube 66, such as of a resilient plastic or rubber. The IV system includes an IV solution source or bottle indicated at 68 which supplies the solution to tube 64 through a conventional drip chamber 70 and a suitable or conventional drip control valve 72. Thus, flow controlled liquid flows from the I.V. solution source 68 to the vein 58 of the patient.

The female Luer lock connector 52, which may be, for example, of plastic such as polyethylene or polypropylene, has a Luer tapered inner surface 74 frictionally receiving Luer tapered surface 22 of male connector 18. The right or proximal end of connector 52 is provided with a pair of conventional radially outwardly extending Luer lock tabs or lugs 76 and 78 which are threaded into threads 26 of connector 14 to lock the connector 52 in fluid tight connection with the outer Luer tapered surface 22 of connector 18.

The Luer tapered outer surface of male Luer slip connector 62 is connected to connector 16 by inserting it into opening 42 of resilient locking member 40 and into tight frictional engagement with Luer tapered surface 30 of female connector 28. The connector 16 is rotated into the connector 28 to obtain a good connection. During insertion of male connector 62, the fingers 50 are resiliently moved outwardly allowing the connector 62 to move into bore 30. However, any force tending to move member 62 rightwardly or away from connector 28 causes the inner edges of the fingers 50 to dig or bite into and frictionally prevent such movement. In this way, once the member 62 is inserted into frictional fluid tight connection with Luer tapered bore 30, the member 62 is locked in place by resilient member 40. The member 62 may be of plastic such as polyethylene or polypropylene.

It is seen that both the connector 62 and the infusion catheter 54 are connected in locked fluid communication with each other through the fluid coupler 10. The opening 42 in locking member 40 is sized to frictionally engage the outer surface of a standard male Luer connector such as member 62 when it is in fluid tight engagement with bore 30. Since the fingers 50 are tapered inwardly toward the connector 28, they provide a high bending resistance to provide good locking force against any force tending to move the member 62 rightwardly relative to coupler 10. Preferably, the locking member 40 is rotatably mounted in the walls 32 so that when the male connector such as connector 62 is rotated into frictional engagement with bore 30, the locking member 40 rotates with it.

The coupler 10 may alternately be employed, as shown in FIG. 4, to connect a needle cannula assembly 82 in fluid communication with a plastic syringe 84 having a conventional male, plastic, connector or Luer slip syringe tip 86 similar to connector 62 of FIG. 3. The syringe also has a syringe plunger 87. The syringe tip is inserted through the locking member 40 and into frictional engagement with the Luer tapered surface 30 in the same way connector 62 of FIG. 3 is inserted. The fingers 50 of member 40 bite into the plastic syringe tip 86 to lock it in place.

The needle assembly 82 includes a hypodermic needle or cannula 88 connected to a needle hub 90 having a female Luer lock connector 92 similar to connector 52 of FIG. 3. The connector 92 is inserted into fluid tight locking engagement with Luer slip connector 18 in the same manner as connector 52 is connected to the fluid coupler 10. Thus, when the plunger 87 is moved to pressurize liquid in the syringe 84, fluid flows from the syringe through bores 30 and 20, and through needle 88.

It is seen that the coupler 10 can be used as an adapter to convert a Luer slip connector of a device, such as I.V. connector 62 or syringe 84, to a Luer lock connector. Such a Luer lock connector avoids the danger of a fluid leak occuring during use of the apparatus.

Good results were obtained when the body 12 was molded of polypropylene and the thickness of the female connector 28 averaged about 0.03 inch. In this way the connector 28 is sufficiently flexible to permit a good fluid tight connection between it and a male Luer slip connector, even if there is some misalignment with locking member 40 due to manufacturing tolerances. In this way, the female Luer connector 28 can move or bend from its normal alignment with the opening 42 of member 40, that is, it can bend or pivot so that its longitudinal axis is angular to its normal axis, if necessary, when receiving a male Luer connector.

The male connector retaining or locking member 40 may be made of stainless steel sheet that is, for example, about 0.01 inch thick. The unitary plastic body 12 economically includes the connectors 14 and 28, and the outer wall 32, all of which are internally formed. The outer surface of wall 32 of device 10 is shown formed with longitudinal ribs providing a good gripping surface when making a connection.

As various changes could be made in the above disclosure and drawing without departing from the scope of the invention, it is intended that all matter contained in the above description and apparatus shown in the accompanying drawing shall be interpreted as illustrative and not in a limiting sense.

We claim:

1. A medical fluid coupler for connecting a first device having a female Luer lock connector to a second device having a male Luer slip connector comprising a body having a bore and including a male Luer lock connector at one end of said body for connecting the female Luer lock connector of the first device in fluid tight locking connection with said body and said bore, and another connector at the opposite end of said body including a female Luer slip connector having a Luer tapered bore in fluid communication with said first named bore for receiving the male Luer slip connector of the second device in fluid tight connection therewith and with said bore, said body having an outer wall surrounding said female Luer slip connector in radial spaced relation therewith, and retaining means connected adjacent said opposite end of said body for frictionally engaging and locking the male Luer slip connector of the second device against movement thereof away from said female Luer slip connector, said female Luer slip connector being flexible to permit limited angular movement thereof from its normal longitudinal axis when the male Luer slip connector is inserted therein.

2. The coupler of claim 1 wherein said body is a unitary member of plastic material, said male Luer lock connector includes a male Luer slip connector integral with said body and said female Luer slip connector, and a collar having locking means thereon for locking engagement with locking lugs of the female Luer lock connector of the first device, said outer wall extending toward said opposite end of said body beyond the free end of said female Luer slip connector, and said retaining means is connected to said wall between said free end and said opposite end of said body for frictional engagement with the male Luer slip connector of the second device.

3. The coupler of claim 2 wherein said retaining means comprises a generally disc-shaped resilient member of metal having a central opening in axially aligned relation with said Luer slip connector, and a generally conical portion having radially inner edges at the opening inclined toward said Luer slip connector for frictionally engaging and locking the male Luer slip connector of said second device in fluid tight engagement with said female Luer slip connector and preventing movement thereof away from the same.

4. The coupler of claim 3 wherein said conical portion has a plurality of circumferentially spaced slits extending outwardly from said central opening to define a plurality of resilient fingers.

5. The coupler of claim 1 or 2 including a plastic male Luer slip connector disposed in said female Luer slip connector in fluid tight connection, and said retaining means has a radially inner edge frictionally engaging the outer surface of said plastic male Luer slip connector.

6. The coupler of claim 5 including a female Luer lock connector connected in fluid tight connection with said male Luer lock connector.

7. A fluid coupler for connecting a first device in fluid communication with a second device having a male luer slip connector, said coupler comprising a body having a bore, and including means at one end thereof for connecting a first device in fluid communication with said bore, and connector means at the opposite end of said body for connecting a male luer slip connector of a second device in fluid communication with said bore, said connector means including a female luer connector having a luer tapered bore connected with said first named bore for receiving the male luer connector in fluid tight sealing engagement therewith to thereby connect the second device in fluid communication with said first named bore, one end of said luer tapered bore connecting with said first named bore, said body including a generally cylindrical wall surrounding and in radially spaced relation with said female luer connector and extending beyond the opposite end of said luer tapered bore, and retaining means connected to said wall between said opposite end of said luer tapered bore and said opposite end of said body for engaging and locking the male luer slip connector against movement away from said luer tapered bore.

8. The coupler of claim 7 wherein said retaining means includes a resilient member having a resilient portion engageable with the male luer connector when inserted into said luer tapered bore and wherein said resilient portion defines an opening in said resilient member which is in axially aligned relation with said luer tapered bore.

9. A fluid coupler for connecting a first device in fluid communication with a second device having a male luer slip connector, said coupler comprising a body having a bore, and including means at one end thereof for connecting a first device in fluid communication with said bore, and connector means at the opposite end of said body for connecting a male luer slip connector of a second device in fluid communication with said bore, said connector means including a female luer connector having a luer tapered bore connected with said first named bore for receiving the male luer connector in fluid tight sealing engagement therewith to thereby connect the second device in fluid communication with said first named bore, and retaining means connected at said opposite end of said body for engaging and locking the male luer slip connector against movement away from said luer tapered bore, said body including a generally cylindrical wall radially spaced from said female luer connector, the walls of said female luer connector being relatively flexible to compensate for any misalignment between said retaining means and said luer tapered bore.

* * * * *